United States Patent [19]

Rath

[11] Patent Number: 4,636,208
[45] Date of Patent: Jan. 13, 1987

[54] SURGICAL SPONGE

[76] Inventor: Ewald Rath, Geranienstr. 5, 5600 Wuppertal 21, Fed. Rep. of Germany

[21] Appl. No.: 699,167

[22] Filed: Feb. 7, 1985

[30] Foreign Application Priority Data

Oct. 5, 1984 [DE] Fed. Rep. of Germany ....... 3436471
Jan. 12, 1985 [DE] Fed. Rep. of Germany ....... 3500842

[51] Int. Cl.$^4$ ............................................. A47L 17/08
[52] U.S. Cl. .................... 604/378; 604/362; 604/374; 604/377; 15/210 R
[58] Field of Search ................. 604/55, 374, 377, 362, 604/378; 15/210 R

[56] References Cited

U.S. PATENT DOCUMENTS

| | | | |
|---|---|---|---|
| 358,610 | 3/1887 | Hartmann | 604/374 |
| 810,136 | 1/1906 | Green | 604/374 |
| 2,740,405 | 4/1956 | Riordan | 604/362 |
| 2,972,350 | 2/1961 | Deker | 604/362 |
| 4,068,666 | 1/1978 | Shiff | 604/362 |
| 4,095,542 | 6/1978 | Hirschman | 604/377 |
| 4,214,341 | 7/1980 | Rath | 15/210 R |
| 4,309,997 | 1/1982 | Donald | 604/55 |
| 4,360,013 | 11/1982 | Barrows | 604/55 |
| 4,393,871 | 7/1983 | Vorhauer | 604/55 |

Primary Examiner—C. Fred Rosenbaum
Assistant Examiner—Sherri E. Vinyard
Attorney, Agent, or Firm—Antonelli, Terry & Wands

[57] ABSTRACT

A surgical sponge comprises a bulbous jacket of at least two superimposed inside and outside lying separate cuts of about the same length, of which the outside cut consists of a gauze material, the superimposed cuts having their edge portions gathered together to form a constricted inturned tubular neck, a rubber ring disposed interiorly of the jacket and contracted onto the inturned neck.

The inside lying cut includes of a soft flat fleece of high absorbency, whereby the sponge can be mechanically produced, and is completely homogeneous, soft and nestling and especially the rubber ring is upholstered at its outer side by the soft fleece material. The sponge is free of loose threads and lint and resistant even in moist condition.

13 Claims, 10 Drawing Figures

SURGICAL SPONGE

The invention relates to a surgical sponge comprising a bulbous jacket of at least two superimposed inside and outside lying seperate cuts of about the same length, of which the outside cut consists of a gauze material, with the superimposed cuts having their edge portions gathered together to form a constricted tubular neck, which neck is turned radially inwardly of the jacket and forms a filling core of the sponge, and with a rubber ring disposed interiorly of the jacket and contracted onto the inturned neck thereof retaining it in the constricted inturned position.

Surgical sponges or tampons with an outer cut of gauze are used mainly for surgical interventions on humans or animals. Since surgical sponges or tampons are used for ridding and cleaning wounds and places of surgery of blood and secretions, they must be absorbent, not dissolve and must not leave threads or lint in the wound. On the other hand, the sponges or tampons must be slack and softly nestling for a careful treatment of wounds.

In, for example, U.S. Pat. No. 4,214,341, surgical sponges are proposed which include two cuts tucked in to form a bag with an inturned edge bound by a rubber ring, with both of the cuts being made of a gauze fabric. By tucking in the edges of the proposed sponges, loose threads or lint at the edges of the cuts are put to the inside, so as to prevent a dislodgement of the threads or lint by the double layer. A further advantage of the making up of two gauze layers and the turning-in of the edges through a rubber ring is the possibility of a mechanical production. Nevertheless those sponges of gauze are absorbent only in a limited way and in the area of the rubber ring, i.e. at the mouth of the bag, there is a quite firm zone, because the rubber ring is not sufficiently covered by the two gauze layers and the two layers are pressed together by the rubber ring and therefore form a lot of firm crinkles.

In, for example, U.S. Pat. No. 2,716,408, a surgical sponge is proposed which is also readily adaptable to a mechanical production. This proposed sponge includes an outer cut of gauze the edge portions of which are tucked in through a rubber ring. The central portion of the outer cut forms a bag stuffed by a spherical ball or core of cotton fibers. A disadvantage of this proposed sponge resides in the fact that, since the portion of filling cotton fibers forming the spherical ball or core have to be plucked from a large size cotton bale, many loose particles and lint are formed which can come out of the ready-made sponge or which may adhere to the outer surface of the sponge. Furthermore, the rubber ring of this proposed sponge must have a minimum diameter for enabling a introduction of the filling core so that the mouth of the bag is not completely closed and, therefore, loose fibers and lint can come out of the mouth of the sponge. After all the firm rubber ring is quite sensible, since it is covered by only one layer of gauze.

Furthermore the use of fleeces of paper or fabric is known for household purposes. Those fleeces are highly absorbent; but their chafing resistence and their tensile strength are, especially in moist condition, so low that some particles can easily loosen and thus their use for medical purposes is absolutely impossible.

Finally, there are known further surgical sponges by the U.S. Pat. No. 2,400,250, U.S. Pat. No. 2,740,405, U.S. Pat. No. 2,755,805, U.S. Pat. No. 2,829,648, U.S. Pat. No. 3,089,495 and U.S. Pat. No. 3,190,289.

An important object of the present invention resides in providing a surgical sponge which is highly absorbent, which at the same time, is free of loose threads and lint, supple, and resistant even in moist condition, which sponge can be mechanically produced, and completely homogeneous, soft and nestling.

According to advantageous features of the invention and inside lying cut includes a soft flat fleece of high absorbency, whereby the bulbous jacket as well as the filling core are each made up of gauze and of fleece material, and the rubber ring is upholstered at its outer side by the soft fleece material.

A further object of the invention resides in the provision of a surgical sponge a diameter of which can be easily varied. Especially for veteriany purposes there is a need of very great diameters of, for example, at least 100 millimeters.

According to further features of the invention, the inside lying cut includes a flat, compressible surgical wadding fleece, with a preferred range of thickness of the inside lying cut being in the range of 2 to 8 mm, and an inner diameter of the rubber ring is nearly twice or thrice greater than the thickness of the uncompressed surgical wadding fleece.

Another object of the invention resides in providing a surgical sponge with the above mentioned qualities, which, at the same time, has a projecting cord safely fixed at the inside of the sponge so that the sponge can be withdrawn from hardly accessible places of surgery.

A still further object of the present invention resides in the provision of a surgical sponge with the above mentioned characteristics which at the same time is X-ray detectable.

The invention will be explained in more detail on the basis of several embodiments shown by way of examples in the drawing.

Figure 1:
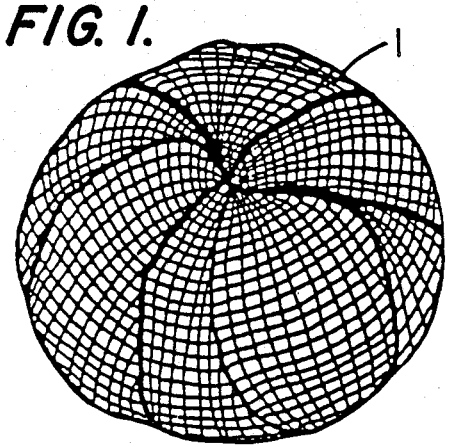
FIG. 1 is a perspective view of a first embodiment of a surgical sponge according to the invention.
Figure 2:
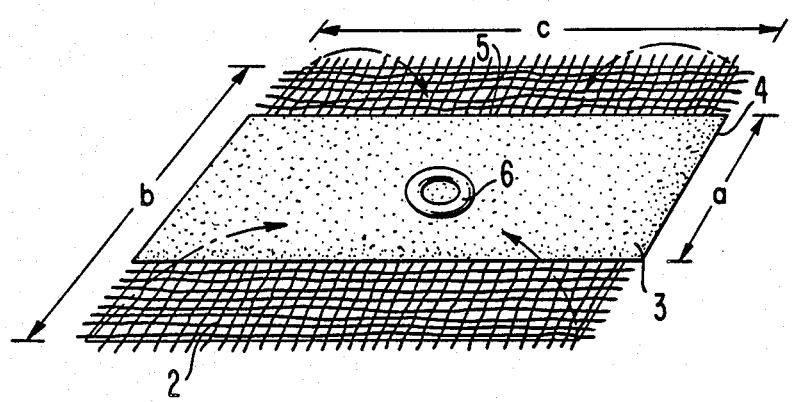
FIG. 2 shows, to a reduced scale, spread out flat, and placed one upon the other, two cuts of an outer gauze fabric and an inner paper fleece in a perspective view.
Figure 3:
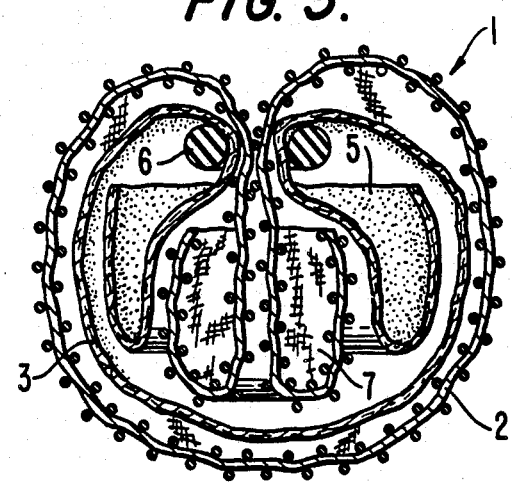
FIG. 3 is a section through the ready-made sponge according to FIG. 1.

Referring now to the drawings wherein like reference numerals are used throughout the various views to designate like parts and, more particularly, to FIG. 1, according to this figure, a first embodiment of a surgical sponge 1 is folded into a small ball and made of an outer cut 2 of gauze and an inner cut 3 of paper fleece. The cuts 2, 3 are, as shown in FIG. 2, of an equal length c. The outer cut 2 of gauze has a width a. By varying the width a, the shape of the sponge 1 can be adjusted between an egg-shaped and a ball. By choosing a sufficient width a of about at least ⅔ of b, it is possible that not only the longitudinal edges 4, but also the lateral edges 5 of the inner fleece cut 3 can be tucked in through the rubber ring 6. FIG. 3 shows a section through the ready-made sponge 1 with completely in-tucked lateral edges 4, 5 of the inner fleece cut 3.

Because of the inner paper fleece cut 3, the sponge 1 is highly absorbent. The low chafing resistance and the low tensile strength of moist fleece have no negative effects on the use of the surgical sponge 1, because the inner fleece cut 3 is completely covered by the outer gauze cut 2. In this way the outer gauze cut 2 takes over all the using effects of traction and rubbing-down whereas the inner fleece cut 3 is only exposed to compression. If, by way of exception, the fleece cut 3 is nevertheless slightly damaged, e.g. ripped, the loosened particles immediately cling to the adjacent moist fleece so that they cannot penetrate the outer gauze cut 2 and, for example dirty a wound. Even after a long, intensive rubbing of the moist sponge, as normally never occurs in practical treatment of wounds, no particles of fleece come out of the sponge 1.

Preferably, the material of the inner cut 3 is a fleece of non-glued paper fibers, which has a very high absorbency. Therefore the inner cut 3 can be of a quite low thickness from 0.05 to 1.0 mm (i.e. from 0.03 to $0.6 \times 1/16$ in) to achieve a sufficient absorbency and at the same time a good flabbiness, i.e. a high nestling quality of the sponge 1. Moreover a non-glued paper fleece is very soft so that there is a sensible upholstering effect on the rubber ring 6.

The edge portions of the outer cut 2, tucked in through the rubber ring 6, form a core 7 at the inside of the sponge 1, with the core 7 maintaining the elasticity of the sponge 1 even after the moistening of the inturned edge portions of the paper fleece cut 3 which constitute a further part of the filling material of the sponge 1.

The complete turning-in of the edges 4, 5 of the inner cut 3 is especially advantageous, if the inner cut 3 is formed of a very coarse paper fleece material, because there is a certain risk of loosening of particles at the edges 4, 5. The penetration of such particles is safely prevented by the double layer 2, 3 at all sides of the sponge 1.

The surgical sponges of gauze according to the prior art in general need 20 threads per square centimeter, (i.e. 130 threads per square inch), i.e. 12 warp threads and 8 weft threads, in order to achieve a sufficient absorbency. The sponge 1 has so an excellent absorbency of the inner paper fleece cut 3 that the outer gauze cut 2 can have a reduced density of threads in the range from 15 to 18 threads per square centimeter. With a density of e.g. 17 threads per square centimeter, that is 10 warp threads and 7 weft threads, it is still ensured that even in moist condition no particles of fleece can penetrate to the outside.

The characteristics of the sponge 1 can be improved by replacing the inner cut 3 by several layers of paper fleece cuts. This special embodiment is not shown in the drawing. As the flexural stiffness of a single layer is higher than that of several separate layers of the same total thickness a higher nestling quality with an unchanged high absorbency is achieved by this step.

Figure 4:
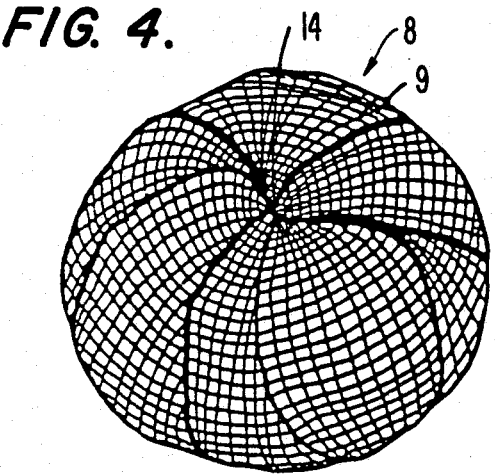
FIG. 4 is a perspective view of a second embodiment of a surgical sponge.
Figure 6:
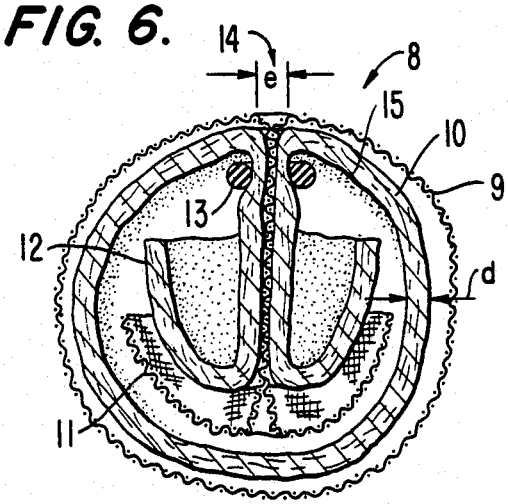
FIG. 6 is a section through the sponge according to FIG. 4.
Figure 5:
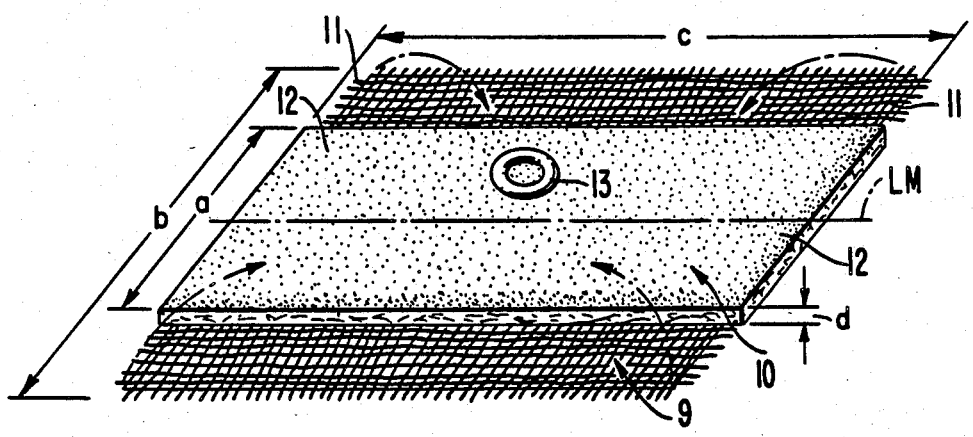
FIG. 5 shows, spread out flat and placed one upon the other, two cuts of an outer gauze fabric cut and an inner wadding fleece cut the two cuts being prepared for the production of a sponge according to FIG. 4.

FIGS. 4, 5 and 6 illustrate a second embodiment of a surgical sponge 8 folded into a ball and including an outer cut 9 of a gauze fabric and an inner cut 10 of a flat, compressible surgical wadding fleece. According to FIG. 4, the two cuts 9, 10, lying one upon the other, are cut to length at the same time and, therefore, have the same length c. The outer cut 9 of gauze has a width b, the inner cut 10 has a smaller width a. For the production of the sponge 8, the edge portions 11, 12 of the outer cut 9 and the inner cut 10 are turned in through a rubber ring 13 forming a constricted tubular neck and a filling core of the sponge 8. In FIG. 6, the core is only slightly outlined for reasons of clarity of the drawing.

The inner compressible wadding fleece cut 10 is of a great thickness d in the range from 0.5 to 10 mm (i.e. from about 0.3 to $6.0 \times 1/16$ in) with a weight per unit area from 50 to 500 grams per square meter, i.e. from 1.5 to 15 ounce per square yard. By the choice of the thickness d of the inner cut 10, the diameter of the sponge 8 can be varied within a wide range. The greater sponge diameters of about 100 mm (i.e. 3.9 in) or even more refer to a cut thickness d of 10 mm and a weight per unit area of about 500 grams per square meter; the smaller sponge diameters from 20 to 25 mm (i.e. about 1 in), refer to a cut thickness d of about 2 mm and a weight per unit area of 50 grams per square meter.

By the choice of the weight per unit area and, in combination with the thickness, of the packing density, the characteristics of the sponge 8 can be influenced, especially concerning its absorbency, its elasticity and its softness.

A sponge 8 of the wide-spread diameter of 4 or 5 cm preferably is of a thickness d from 3 to 5 mm and of a weight per unit area from 70 to 150 grams per square meter.

Considering the ready-made sponge 8 according to FIG. 5 the inner diameter e of the rubber ring 13 is approximately twice or thrice greater than the thickness d of the uncompressed wadding fleece cut 10. Thus, the two cuts 9, 10 are gathered in a quite small area the two cuts 9, 10 forming a lot of crinkles and the inner wadding fleece cut 10 additionally being compressed to about one tenth of the uncompressed thickness d. This crinkling and compressing, especially of the wadding fleece cut 10, could be outlined in FIG. 5 only in a symbolic way; but the crinkling of the outer gauze cut 9 concentrated at the mouth 14 of the bag is clearly illustrated in FIG. 4.

Next to the rubber ring 13, this is at the mouth 14 of the sponge 8, the inner wadding fleece cut 10 swells and decrinkles, thus assuming an uncompressed thickness d within a short distance. In this manner, a very soft, fungiform or mushroom-shaped zone 15 is formed, upholstering the rubber ring 13 in a really surprising way. Thus, the sponge 8 is homogeneous at all sides and can be introduced in a wound in any orientation.

Because of the compressed wadding fleece cut 10, the mouth 14 of the sponge 8 is tightly closed so that no loose lint or particles of wadding can come out. Furthermore, the surface of the inturned edge portions 12 of the inner wadding fleece 10 is completely covered by the edge portions 11 of the gauze cut 9 forming an inwardly turned tubular neck.

Even on producing the sponge 8 there are only a few loose particles because the portioning of the filling core is made by a simple cut of a flat band of wadding fleece, as clearly shown in FIG. 6, and not by a plucking of a wadding bale.

Figure 7:
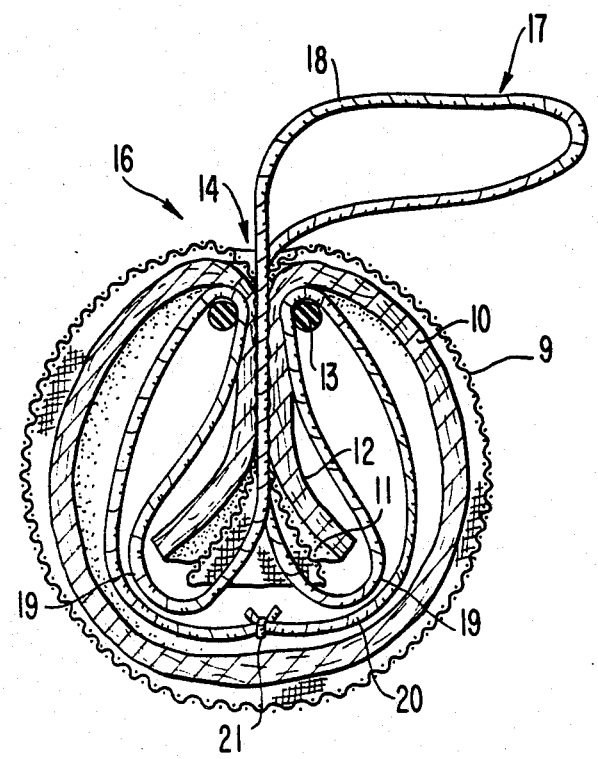
FIG. 7 is a section through a third embodiment of a sponge with a safety cord.

In FIG. 7, a surgical sponge 16 made up, by analogy to the sponge 8, of an outer cut 9 of gauze and an inner cut 10 of a surgical wadding fleece. The cuts are turned in through a rubber ring 13 to form a bag. The sponge 16 additionally has a safety cord 17 in form of a knotted, closed loop with a gripping sling 18 projecting out of the mouth 14. Inside of the sponge 16 the gripping sling 18 is connected to two slings 19 for gathering up the inturned edge portions 11, 12 of the cuts 9, 10. The gripping slings 19 are linked up with a fixing sling 20 extending around the rubber ring 13 at the side of the mouth 14. Thus, the safety cord passes through the rubber ring 13 a total of four times. The ends of the safety cord 17 are joined by a knot 21 placed at the bottom of the bag and upholstered at all sides. On pulling the gripping sling 18 the edge portions 11, 12 are gathered up by the gripping slings 19 and form a stopper safely fixing the cord 17 by the fixing sling 20. The sponge 16 can be produced in a very easy way. More particularly, before the turning-in of the edge portions 11, 12, the knotted cord 17 is drawn around the two cuts 9, 10, spread out flat according to FIG. 5, the cord 17 orientated along the longitudinal center line LM and the knot 21 placed onto the upper side of the wadding fleece cut 10 beneath the rubber ring 13.

Figure 8:
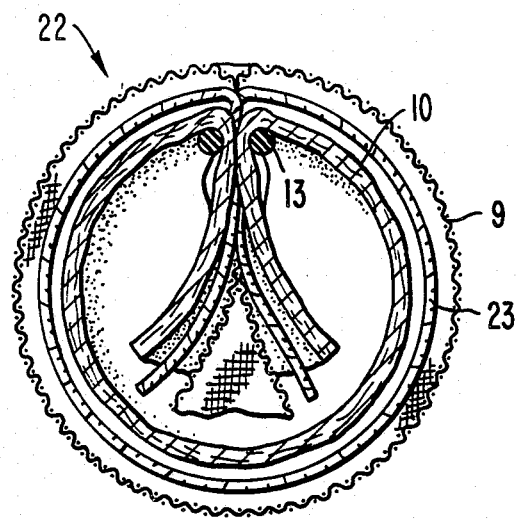
FIG. 8 is a section through a fourth embodiment of an X-ray detectable sponge.
Figure 9:
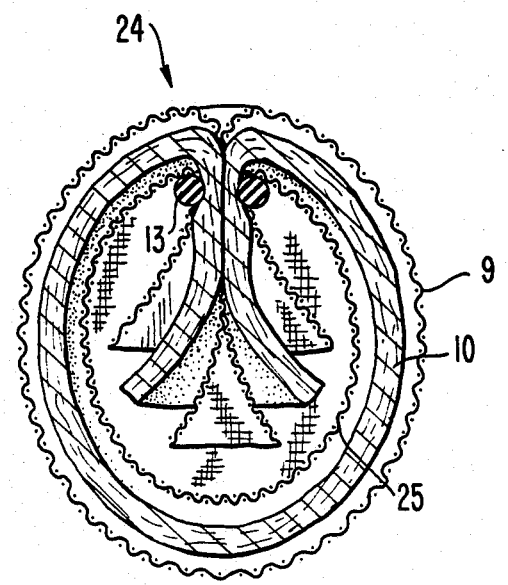
FIG. 9 is a section through a fifth embodiment of a sponge with a further inner layer of gauze.
Figure 10:
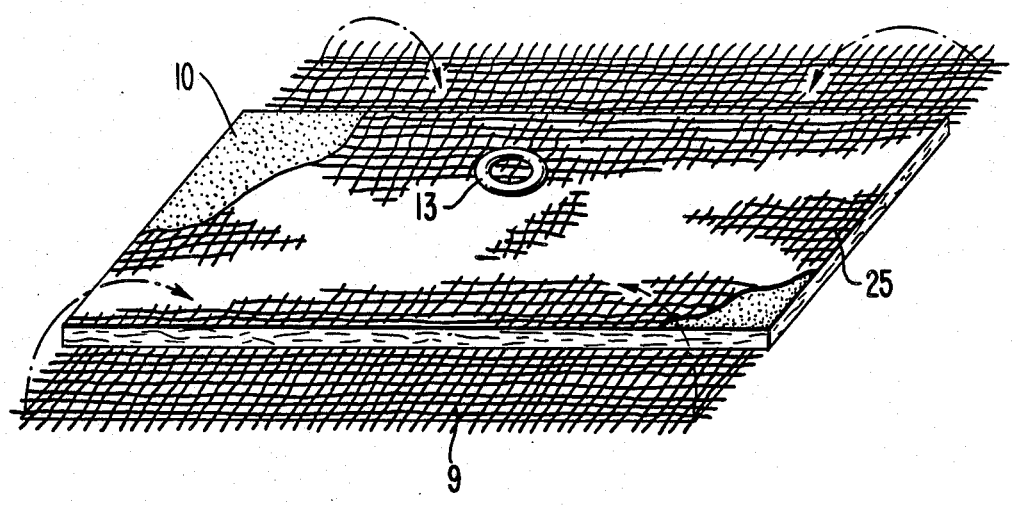
FIG. 10 shows, spread out flat and placed one upon the other, three cuts for the production of a sponge according to FIG. 9.

In FIG. 8, a surgical sponge 22 is illustrated which includes an outer gauze cut 9, an inner surgical wadding fleece cut 10 and a rubber ring 13. A X-ray detectable thread 23 is disposed between the inner and the outer cuts 9, 10 so that the sponge 22 is adapted for complicated surgical interventions. A sponge with a X-ray detectable thread is proposed in U.S. Pat. No. 2,972,350, but this proposed sponge is inhomogeneous and the X-ray-thread is not visible with the naked eye. Therefore, in practical use sponges with and without X-ray detectable threads can easily be confounded.

The embodiment of FIG. 6 shows a further embodiment of a surgical sponge 24 comprising an outer gauze cut 9 and an inner surgical wadding fleece cut 10 tucked in through a rubber ring 13 to form a bag. At the inside of the sponge 24, there is a further cut 25 of gauze so that the wadding fleece cut 10 is covered at both its surfaces. For the production of the sponge 24 the three cuts 9, 10, 25 have to be laid one upon the longitudinal central axis of the other and then turned in through the rubber ring 13. As the wadding fleece cut 10 is covered at both its surfaces by the gauze cuts 9, 25, the three cuts 9, 10, 25 can be wound onto a coil without a clinging between the different threefold layers. Therefore the mechanical production, especially the supply of cuts, is much simplified.

By virtue of the features of the present invention as described hereinabove, it is possible to provide a surgical sponge which may be manufactured at a reasonable cost.

While I have shown and described several embodiments in accordance with the present invention, it is understood that the same is not limited thereto but is susceptible of numerous changes and modifications as known to one having ordinary skill in the art, and I therefore do not wish to be limited to the details shown and described herein, but intend to cover all such modifications as are encompassed by the scope of the appended claims.

I claim:

1. A ball-shaped surgical sponge for medical purposes, the surgical sponge comprising a bulbous jacket of at least two superimposed inside and outside lying separate cuts of substantially the same length, of which the outside lying cut is of a gauze material, the superimposed cuts having their edge portions gathered together to form a constricted tubular neck, said tubular neck being turned radially inwardly of the jacket and forming a filling core of the sponge, a rubber ring disposed interiorly of the jacket and contracted onto the inturned neck thereof retaining it in the constricted inturned position, wherein said inside lying cut consists of a soft flat fleece of high absorbency, whereby the bulbous jacket as well as the filling core are each made up of gauze and of fleece material, and wherein said rubber ring is upholstered at its outer side by the soft fleece material.

2. A surgical sponge as claimed in claim 1, wherein the inside lying cut includes a fleece of non-glued paper fibers.

3. A surgical sponge as claimed in claim 2, wherein the inside lying cut is of a thickness from 0.05 to 1.0 millimeters.

4. A surgical sponge as claimed in claim 2, wherein the inside lying cut includes several layers of paper fleeces.

5. A surgical sponge as claimed in claim 1, wherein the inside lying cut includes synthetic wool fleece made of cellulose.

6. A surgical sponge as claimed in claim 1, wherein the gauze of the outside lying cut includes only 15 to 18 threads per square centimeter.

7. A surgical sponge as claimed in claim 1, wherein said inside lying cut includes a compressible surgical wadding fleece.

8. A ball-shaped surgical sponge for medical purposes, the surgical sponge comprising a bulbous jacket of at least two superimposed inside and outside lying separate cuts of substantially the same length, of which the outside lying cut is of a gauze material, the superimposed cuts having their edge portions gathered together to form a constricted tubular neck, said tubular neck being turned radially inwardly of the jacket and forming a filling core of the sponge, a rubber ring disposed interiorly of the jacket and contracted onto the inturned neck thereof retaining it in the constricted inturned position, wherein said inside lying cut includes a flat, compressible surgical wadding fleece having a thickness in the range from 0.5 to 10 mm and a weight per unit area from 50 to 500 grams per square meter.

9. A ball-shaped surgical sponge for medical purposes, the surgical sponge comprising a bulbous jacket of at least two superimposed inside and outside lying separate cuts of substantially the same length, of which the outside lying cut is of a gauze material, the superimposed cuts having their edge portions gathered together to form a constricted tubular neck, said tubular neck being turned radially inwardly of the jacket and forming a filling core of the sponge, a rubber ring disposed interiorly of the jacket and contracted onto the inturned tubular neck thereof retaining it in the constricted inturned position, wherein said inside lying cut includes a flat, compressible surgical wadding fleece and wherein a preferred range of thickness of the inside lying cut is from 2 to 8 mm, and an inner diameter of said rubber ring is approximately at least twice that of the thickness of said uncompressed surgical wadding fleece cut.

10. A surgical sponge as claimed in claim 9, wherein for sponges of a diameter from four to five centimeters the weight per unit area is from 70 to 150 grams per square meter.

11. A surgical sponge as claimed in one of claims 7 or 9, wherein the cut of surgical wadding fleece is embedded between two gauze cut layers.

12. A surgical sponge as claimed in one of claims 2 or 7, further comprising a safety core in a form of a knotted closed loop which includes a gripping sling projecting out of a neck of the jacket, two gathering sling means for gathering the inturned edge portions of the cuts, and a fixing sling means inside of the jacket for connecting said gathering sling means, wherein the safety cord passes through the rubber ring four times.

13. A surgical sponge as claimed in one of claims 2 or 7, wherein a X-ray detectable thread lies between the inside and the outside lying cuts.

* * * * *